United States Patent [19]
Walinsky

[11] Patent Number: 5,470,314
[45] Date of Patent: Nov. 28, 1995

[54] PERFUSION BALLOON CATHETER WITH DIFFERENTIAL COMPLIANCE

[76] Inventor: Paul Walinsky, 8910 Carlisle Rd., Wyndmoor, Pa. 19038

[21] Appl. No.: 279,061

[22] Filed: Jul. 22, 1994

[51] Int. Cl.⁶ .................................................. A61M 29/00
[52] U.S. Cl. ............................ 604/96; 604/99; 604/104; 604/282
[58] Field of Search ................................. 604/96, 99, 103, 604/104, 93, 264, 280, 282

[56] References Cited

U.S. PATENT DOCUMENTS

| | | | |
|---|---|---|---|
| 4,183,102 | 1/1980 | Guiset | 604/101 |
| 4,637,396 | 1/1987 | Cook . | |
| 4,796,629 | 1/1989 | Grayzel | 606/194 |
| 4,909,252 | 3/1990 | Goldberger | 606/194 |
| 4,944,745 | 7/1990 | Sogard et al. | 606/194 |
| 5,108,370 | 4/1992 | Walinsky | 606/194 |

Primary Examiner—Corrine M. Maglione
Assistant Examiner—N. Kent Gring
Attorney, Agent, or Firm—William H. Meise

[57] ABSTRACT

A perfusion balloon catheter (10), as for angioplasty by dilatation, has the balloon (30) formed so that, when inflated within a vas or coronary artery, one or more channels (40) are provided for the flow of bodily fluids or blood past the inflated balloon. In one embodiment, the balloon has a toroidal shape which defines a central open channel. In order to avoid closure of the central channel when the balloon inflation pressure is increased to distend the vas within which it is placed, a portion (44) of the balloon is made from a relatively elastic membrane, and the portion of the balloon (244) adjacent the channel (40) is made from a relatively less elastic material, or a rigid material, whereby additional pressure does not cause channel closure.

15 Claims, 6 Drawing Sheets

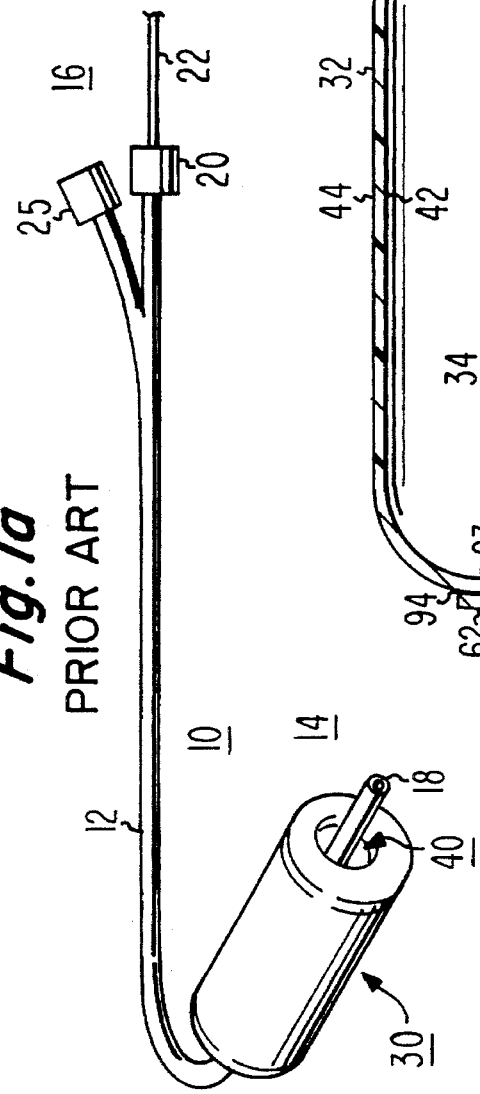
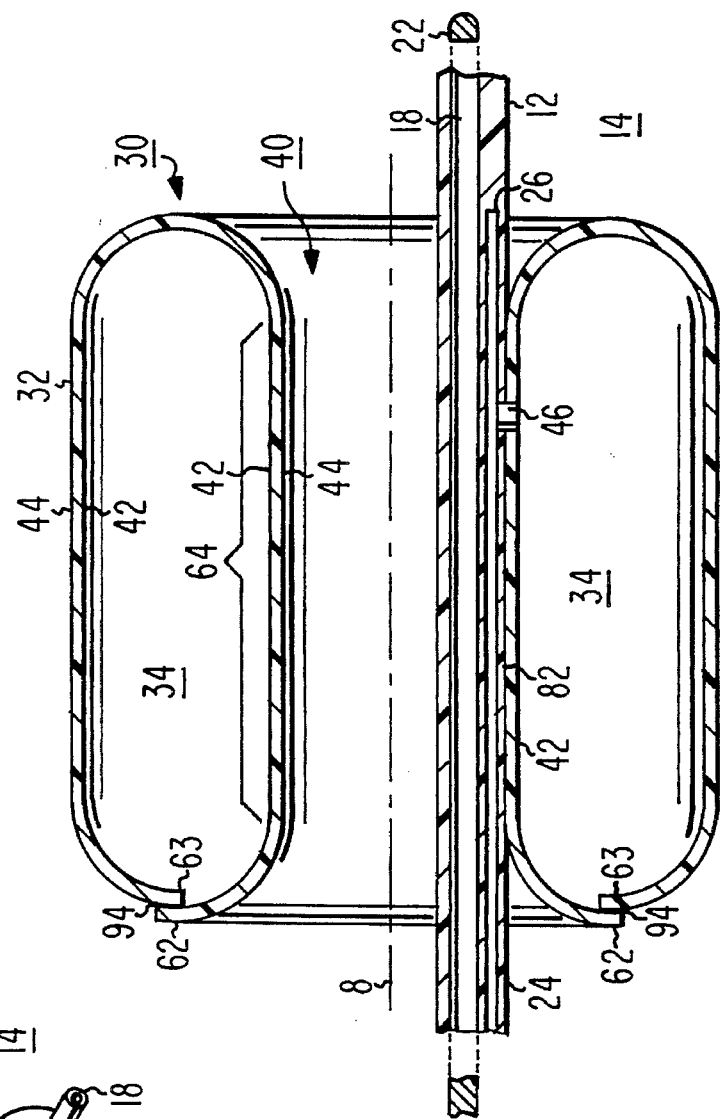
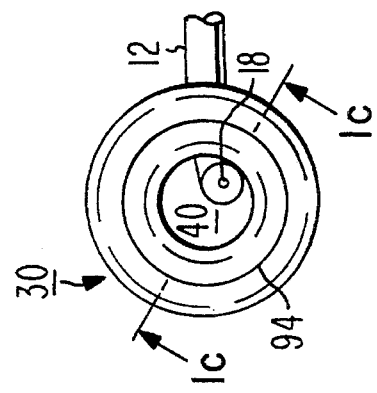

1

PERFUSION BALLOON CATHETER WITH DIFFERENTIAL COMPLIANCE

This invention relates to balloon catheters for angioplasty, and particularly to perfusion balloons, which allow blood flow past the inflated balloon.

In general, an angioplasty procedure is performed by obtaining access to the interior of the affected coronary artery, and advancing a deflated balloon to the location of the stenosis. The balloon is inflated by applying fluid pressure through an inflation/deflation ("inflation") lumen of the catheter, to thereby apply balloon pressure tending to expand the lumen of the coronary artery. When the stenotic portion of the lumen of the blood vessel or coronary artery has about the same diameter as adjacent portions which are free from plaque, the procedure may be terminated, the balloon deflated and the catheter removed. It has been observed, as in the article entitled "Perfusion During Coronary Angioplasty," by Rossen, published at pages 103–106 in the June 1989 issue of Cardio, that increased time with the balloon inflated is associated with an improved result.

Those portions of the heart muscle supplied with blood flow through the artery are partially deprived of blood flow when the catheter with deflated balloon is being positioned in the stenotic region, and may be completely deprived of blood flow when the balloon is inflated. This in turn has a tendency to decrease heart pumping efficiency, and the blood pressure tends to drop. Chest pains result in some patients. Either of these indications may undesirably require early termination of the procedure.

Dilatation catheters are available, as mentioned in the above-mentioned Rossen article, in which perfusion or blood flow past the occluding catheter and balloon is provided by fenestrations or apertures into the distal lumen of the catheter on both sides of the balloon. When the distal lumen is also used for a guide wire, the guide wire must be retracted during perfusion, which requires additional manipulation, and may result in loss of position of the balloon. Further manipulation is required if the guide catheter surrounding the dilatation catheter must also be retracted.

A perfusion balloon catheter is described in U.S. Pat No. 5,108,370, issued Apr. 28, 1992 in the name of Walinsky, which includes an inflatable balloon which, when inflated, itself defines an aperture or channel through which blood may flow while the balloon is inflated. FIGS. 1a, 1b and 1c illustrate an angioplasty dilatation catheter according to the Walinsky patent. In FIG. 1a, a catheter designated generally as 10 includes an elongated portion 12 and a balloon 30. Elongated portion 12 includes a distal end 14 and a bifurcated proximal end 16. Elongated portion 12 also includes a distal lumen 18 which extends from an open end at distal end 14 to an access aperture 20 at proximal end 16. Distal lumen 18 is dimensioned to provide a sliding fit for a guide wire, illustrated as 22. Such guide wires at the current state of the art have diameters of about 0.016 inches. The distal end of guide wire 22 may be positioned to extend beyond distal end 14 of elongated portion 12, as illustrated in FIG. 1c.

Also extending within elongated portion 12 of catheter 10 is a balloon inflation/deflation ("inflation") lumen 24, seen in cross-section in FIG. 1c. Balloon inflation lumen 24 extends from an access aperture 25 and within elongated portion 12 to terminate at a location 26, which location is removed from the most distal end of elongated portion 12, but is at or beyond balloon 30.

Balloon 30 includes a membrane 32. As illustrated in FIG. 1, balloon 30 when inflated has a shape which is generally toroidal. A toroid is a 3-dimensional shape formed by the revolution of a plane figure around an axis. In the case of balloon 30, the inflated portion 34 surrounded by membrane 32 as seen in cross-section is the plane figure, which is revolved about a central axis 8. More specifically, in FIG. 1c, the plane figure is the region lying above axis 8, designated 34 and bounded by membrane 32. Such a 3-dimensional shape is generally termed a "solid" of revolution, and this designation is used herein, even though the "solid" portion is actually a hollow balloon.

It should be noted that the shapes of the balloon described herein occur only when the balloon is inflated. When the balloon is deflated, membrane 32 may be wrapped or closely formed about elongated portion 12 of catheter 10. The solid of revolution bounded by membrane 82 defines a central open channel 40. Central channel 40 allows body fluids to flow therethrough. Channel 40 extends through balloon 30 in the sense that body fluids may move axially parallel to catheter 10, but it is helpful to note that the toroidal shape of balloon membrane 32 defines a closed solid figure in which inflated region 34 is bounded by an inner surface 42, while channel 40 through which body fluids may flow is adjacent an exterior surface 44 of membrane 32. Thus, channel 40 does not extend through balloon 30 in the sense that fluids within the balloon co-mingle with body fluids. The use of the term "through the balloon" should be understood in this context.

The exterior diameter of elongated portion 12 of catheter 10 is smaller than the interior diameter of channel 40. The exterior surface of elongated portion 12 is attached to balloon 30 along one side of channel 40, which as illustrated in FIG. 1c is the lower side of channel 40. An inflation/deflation ("inflation") aperture 46 extends through membrane 32 at the point of attachment to provide communication between inflation lumen 24 and balloon interior 34.

It has been discovered that the balloon as described above, when inflated against the walls of a lumen of a vas, may require increased pressure in order to expand the outer portion of the balloon, to thereby distend the vas, against the resistance of the walls of the vas. This increased pressure, in turn, tends to cause that portion of the elastic membrane designated 64, which is adjacent central channel 40, to distend toward the channel, which tends to close off the channel. Such a result is undesirable, as it tends to reduce blood flow.

SUMMARY OF THE INVENTION

A catheter according to the invention includes an elongated portion defining proximal and distal ends, and also defining at least one elongated lumen adapted for the flow of fluid therethrough. The elongated portion has a particular cross-sectional area at a particular location near the distal end. In the case of a circular shape of the elongated portion, the particular cross-sectional area is uniquely related to a particular diameter. A balloon arrangement is coupled at or near the particular location of the elongated portion of the catheter. The balloon arrangement defines a peripheral closure (the structure which contains the balloon pressure, which in an ordinary balloon is the balloon membrane enclosing the pressurized interior) including a relatively elastic (or more compliant) membrane portion and a less elastic (or more rigid) portion. The peripheral closure defines an interior surface which is adjacent the interior of the balloon (where the inflation fluid is contained), and also defines an exterior surface which is adjacent the exterior of the balloon, meaning that the exterior surface is normally in contact with body fluids during use. The balloon is adapted for inflation within a vas and is configured, so that, when inflated within a vas, it defines an open channel adjacent the exterior surface of the membrane, which open channel extends from a distal portion of the balloon to a proximal portion of the balloon. The channel has a cross-sectional area which is greater than the particular cross-sectional area of the elongated portion of the catheter. In the context of a torus with a circular transverse cross-section, the cross-sectional area of the channel has a greater inner diameter than the particular diameter of the elongated portion of the catheter. The elongated portion of the catheter extends through the open channel, and is coupled to the peripheral closure on one side of the open channel, whereby body fluids may flow through that portion of the cross-sectional area of the channel which is not occupied by the elongated portion of the catheter. At least one aperture extends between the elongated lumen defined by the elongated portion and the interior of the balloon, whereby the balloon may be inflated and deflated from the proximal end of the elongated portion of the catheter. In a catheter according to one embodiment of the invention, the peripheral closure of the balloon defines a surface, when the balloon arrangement is inflated, which is substantially toroidal and defines a central opening, which central opening of the toroidal surface defines the open channel through which body fluids, such as blood, may flow. In another embodiment of the catheter, the less elastic portion of the peripheral closure is a substantially rigid tube, the lumen or interior of which defines the open channel, and the exterior of which constitutes at least a portion of the inner surface of the balloon. In an embodiment of the catheter in which the peripheral closure of the balloon arrangement defines a surface which, when the balloon arrangement is inflated, is substantially toroidal and defines a central opening, the elongated portion is attached to the interior of the tube on one side of the central opening of the toroidal surface. In yet another embodiment, the less elastic portion has anisotropic elasticity, meaning that the less elastic portion has elasticity which varies, depending upon the direction in which distension is measured in response to the same applied force or inflation pressure. The less elastic portion may include a reinforced elastic membrane, and the reinforcement may be anisotropic. One type of anisotropic reinforcement may be a plurality of relatively rigid elongated rods, each defining an axis of elongation, which rods are affixed, with their axes of elongation mutually parallel, to the balloon material at the interior of the open channel. Such a reinforced embodiment might also include a relatively inelastic filamentary reinforcement wound about the exterior surface of the balloon, passing repeatedly through the central channel. The relatively elastic membrane portion may be made from polyethylene terephthalate. The reinforcement may be two or more layers of membrane. As an alternative, the reinforced portion of the peripheral closure of the balloon may be a single material of variable thickness, with the thinner portion being relatively elastic, and the thicker portion being relatively rigid. The thickness may be stepped or tapered.

DESCRIPTION OF THE DRAWINGS

FIG. 1a is a perspective or isometric view of a dilatation catheter with toroidal inflated balloon, FIG. 1b is an axial or end view of the inflated balloon, showing the central channel, and FIG. 1c is a cross-section taken through the catheter, showing the balloon attachment region, FIGS. 1a, 1b and 1c are referred together as FIG. 1 prior art;

DESCRIPTION OF THE INVENTION

Figure 2A:
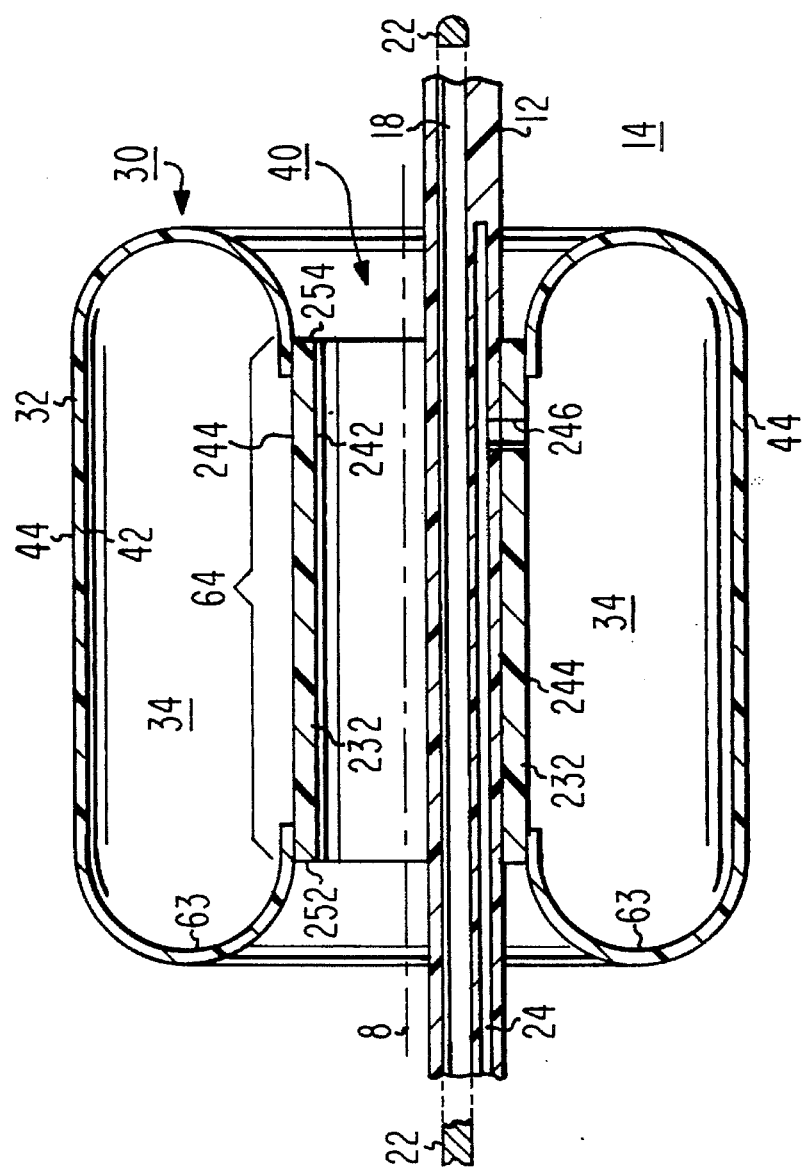
FIGS. 2a and 2b illustrate cross-sectional and end views, respectively, of a dilatation catheter according to the invention, in which a portion of the balloon near the central channel is made from a relatively rigid tube.
Figure 2B:
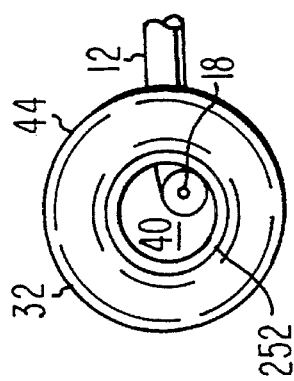

FIGS. 2a and 2b are similar to FIGS. 1a and 1b, except that the balloon 30 has two outer wall or peripheral closure portions, one of which, designated 32 in FIGS. 2a and 2b, is a membrane similar to that of FIGS. 1a and 1b, located remote from central axis 8, and having a thickness established by the dimension between inner surface 42 and outer surface 44. In contrast to the arrangement of FIGS. 1a and 1b, that portion of the balloon closure surrounding central aperture 40 is a relatively rigid tube designated 232. The FIGURES are not to scale, so the difference in thickness may not be apparent therefrom, but tube 232 is substantially thicker, as measured between its inner surface 242 and its outer surface 244, than membrane 32. Membrane 32 is sealingly affixed to tube 232 near the proximal end 252 and the distal end 254 of tube 232, as by the use of fusion or adhesives. The most proximal end of balloon membrane 32 is designated 63. As in the case of the balloon catheter of FIGS. 1a, 1b, and 1c, an aperture, designated 246 in FIG. 2a, extends from inflation lumen 24 of elongated portion 12 of the catheter to the interior 34 of balloon 30. Both portions of the closure, namely the membrane 32 and the tube 232, may both be made from the same material, which may be, for example, polyethylene terephthalate.

As a result of the difference in thickness between inner closure portion (tube) 232 and closure portion (membrane) 32 as described in conjunction with FIGS. 2a and 2b, the inner closure portion, which is adjacent central channel 40, cannot deflect or expand as much in response to inflation pressure as the membrane portion, i.e. it is less "elastic". Consequently, the walls of the channel cannot "bulge" toward each other as much as in the prior art arrangement of FIGS. 1a, 1b and 1c in response to inflation pressure, so greater pressure may be applied to the balloon to overcome resistance of the walls of the lumen of the vas being treated, with reduced danger of closing off of the blood perfusion channel.

As an alternative to making closure portion or tube 232 of FIGS. 2a and 2b thicker than membrane 32, closure portion 232 may be made from a material which is stronger, or more rigid, than the material from which membrane 32 is made. For example, if membrane 32 is made from polyethylene terephthalate, tube 232 may be made from a metal, as for example stainless steel. Of course, the tubular closure portion may be both thicker than the membrane, as described in conjunction with FIGS. 2a and 2b, and also made from a stronger material, if desired.

As so far described, and as illustrated in conjunction with FIGS. 1b and 2b, the second or more rigid portion of the peripheral closure of balloon 30 is a generally right circular cylindrical tube. Of course, the cylinder may, if desired, have a cross-section which is in a shape other than circular, such as oval, polygonal, or even square or triangular, so long as the cross-sectional area is greater than the cross-sectional area of the elongated portion 12 of the catheter which passes therethrough, so that blood may flow through that portion of the central aperture 40 which is not occupied or occluded by the presence of elongated portion 12.

Figure 3A:
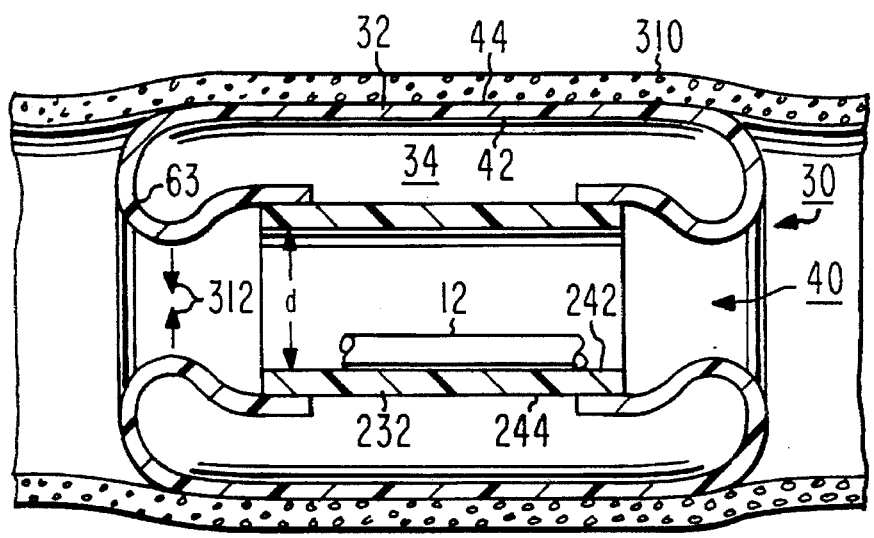
FIG. 3a illustrates in simplified form a problem which may arise when using the catheter as described in conjunction with the arrangement of FIGS. 2a and 2b.
Figure 3B:
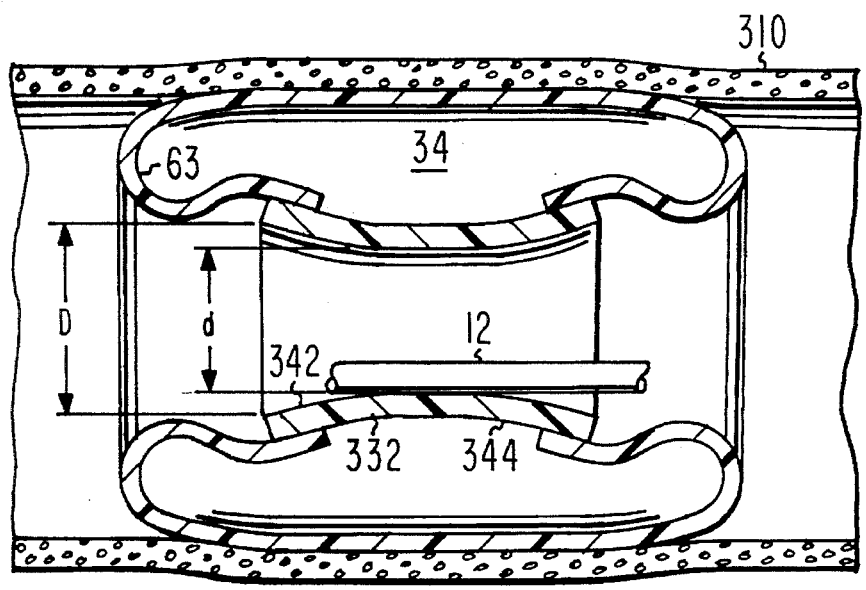
FIG. 3b illustrates a catheter according to the invention, in which the shape of the tube is modified to include trumpet-shaped flanges to reduce the magnitude of the problem.

FIG. 3a illustrates a problem which may occur with an arrangement as described in conjunction with FIGS. 2a and 2b, when the inflation pressure is increased and the outer membrane of the balloon is already pressed against the walls of a lumen of a vas. Elements of FIG. 3a corresponding to those of FIGS. 2a and 2b are designated by the same reference numerals. In FIG. 3a, the walls of the lumen against which balloon 30 presses are designated 310. The proximal portion, which is designated 63, of balloon 30, is distended proximally, and, as a result of losing a portion of its support against radial inward expansion toward axis 8, bulges toward the axis, tending to move the innermost portion of the balloon in the direction of arrows 312. Bulging of portion 63 of membrane 32 in the direction of arrows 312 tends to close off one end of central channel 40, and thereby undesirably tends to reduce the flow of blood. If a balloon bulges on the top and bottom sides by an amount equal to one-half of the inner diameter d of the more rigid tube 232, the channel will be effectively closed. A similar effect occurs at the distal end of the balloon. According to an aspect of the invention, the more rigid tube portion of the balloon peripheral closure is formed into a "bell-mouthed" or "trumpet" shape, which in effect carries the more rigid portion of the balloon peripheral closure toward planes which are perpendicular to the longitudinal axis 8 of the catheter. In FIG. 3b, elements corresponding to those of FIG. 3a are designated by like reference numerals. In FIG. 3b, more rigid portion 332 of the balloon closure is in the shape of a tube with bell mouths at the proximal and distal ends. More specifically, inner surface 342 of more rigid portion 332 of the balloon peripheral closure is tapered, from a lesser diameter d at locations approximately half-way between the proximal and distal ends of the tube, to a larger diameter D near the mouths. The more elastic portion 32 of the balloon peripheral closure is attached to the more rigid portion 332 near the larger-diameter ends, so the bulging, even if it occurs to the same degree as depicted in conjunction with FIG. 3a, starts from locations which are more widely separated or spaced apart, and more pressure may be applied before a like amount of blockage of the central channel occurs. In other words, the balloon bulging starts from locations which are more widely separated than in the arrangement of FIG. 3a.

According to another aspect of the invention, the more elastic portion of the balloon is reinforced by a relatively inelastic filamentary winding, to make the elastic portion of the balloon into more of a "bag" than a "balloon." This is an alternative to the "bell-mouth" arrangement of FIG. 3b, and allows a simple tube to be used, as in FIG. 3a, without excessive bulging, and the resulting closure of the channel.

Figure 4A:
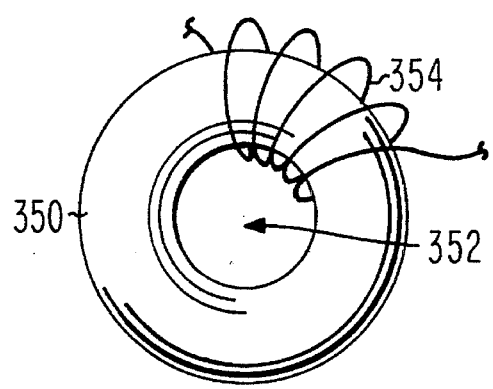
FIG. 4a illustrates a toroidal reinforcing winding about a toroidal balloon.

FIG. 4a illustrates, in its inflated form, a simple toroidal balloon 850 with a central aperture 352, with a few turns of inelastic filament 354 toroidally wound about the balloon. As illustrated in FIG. 4a, the windings are not tightened, and are widely spaced apart, so that the form of the winding may be visualized. When, with the balloon inflated to a particular dimension, the windings are closely spaced to each other about the balloon and tightened against it, the balloon cannot expand further, no matter how much pressure is applied to the interior of the balloon, because the inelastic reinforcing filaments cannot be lengthened to match the increased circumference of the segment of the balloon about which they are wound. Since the circumference of the toroidal segment cannot increase without breaking the filamentary reinforcement, the balloon cannot increase in size. Thus, the balloon membrane is elastic up to a point, beyond which it becomes inelastic due to the reinforcement.

Figure 4B:
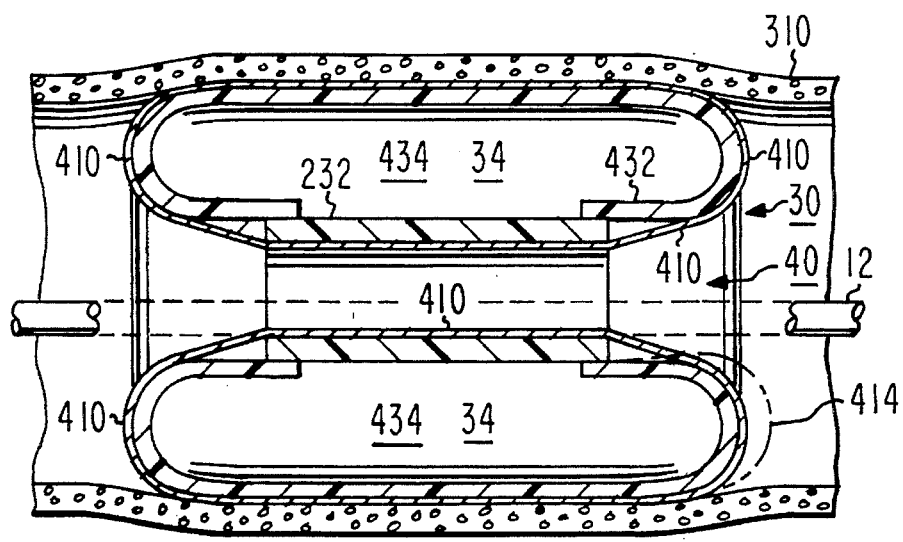
FIG. 4b illustrates a cross-section of the balloon of FIG. 4a, illustrating how such a winding prevents the balloon from bulging excessively.

FIG. 4b is similar to FIG. 3a, but illustrates the effect of reinforcement of the sort described in conjunction with FIG. 4a. In FIG. 4b, the reinforced elastic membrane is designated 432, and the inelastic filamentary reinforcement is illustrated as 410. The cross-sectional area of each half of the balloon interior 34 is designated 434. Once the balloon reaches the point of inflation illustrated in FIG. 4b, it cannot expand further without rupturing the reinforcements. As a consequence, the balloon cannot expand, as suggested, by way of example, by dotted line 414, because the peripheral length of each area 434 must remain equal to the lengths of the reinforcing filament turns. Since the inflation pressure presses the balloon against the surrounding lumen of the vas in which it is used, the proximal and distal ends of the reinforced balloon membrane cannot bulge beyond the limits set by the length of each turn of the reinforcing filament, and therefore resist bulging in a manner which tends to close off the central channel through which blood flows.

Figure 5:
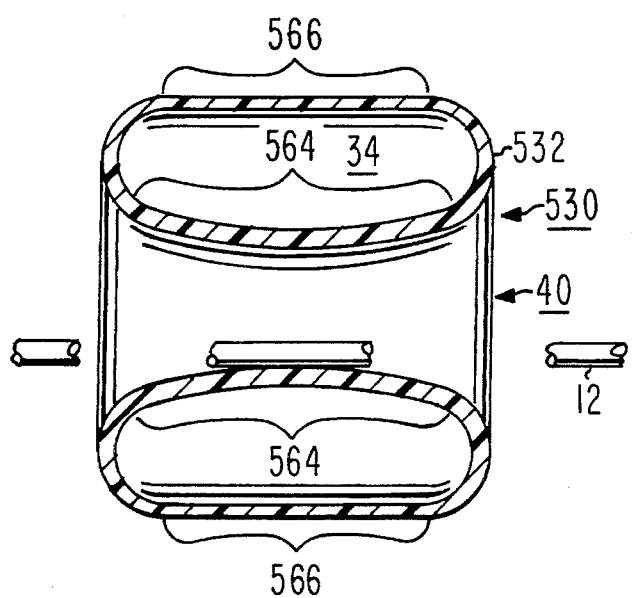
FIG. 5 is a cross-section of a balloon which includes a peripheral closure which consists of a membrane which is of the same material throughout, but which is substantially thicker in a region adjacent the central channel to provide rigidity near the central channel.

As so far described, the peripheral closure of the balloon has included a substantially rigid tube (with or without trumpet-shaped ends), with a membrane which is elastic, at least up to a preset limit imposed by a reinforcement, and which can stretch or expand under the influence of inflation pressure. Since the problem toward which the invention is directed is that of closing of the central channel due to bulging of that portion of the balloon closure adjacent the central channel, the rigidity required of the balloon closure adjacent the central channel to prevent closure will depend upon the pressure difference across the peripheral closure. A rigid tube, as described in conjunction with FIGS. 3a and 3b, will prevent closure regardless of pressure, so long as failure of the material does not occur. However, a rigid tube may be disadvantageous, in that it has a fixed transverse dimension, and cannot be collapsed to a smaller dimension to allow the catheter to be introduced into a vas smaller than the outer dimension of the rigid tube. An intermediate rigidity of the tube, less than completely rigid, but less elastic than the balloon membrane, may be appropriate for many pressure ranges. In FIG. 5, a balloon 530 includes a peripheral closure 532, which consists of a membrane which is of the same material throughout, but which is substantially thicker in a region designated 564 adjacent central channel 40 than in a region designated 566 which, in use, is adjacent the walls of the lumen of the vas. This differential thickness provides the desired difference of elasticity or rigidity, so that the balloon may expand toward the wall of the vas, while expanding inward toward the central channel to a lesser amount. An arrangement using two peripheral closure portions of different elasticities or rigidities, with neither being completely rigid, may allow the balloon to be collapsed, to allow its introduction into a small vas.

Figure 6A:
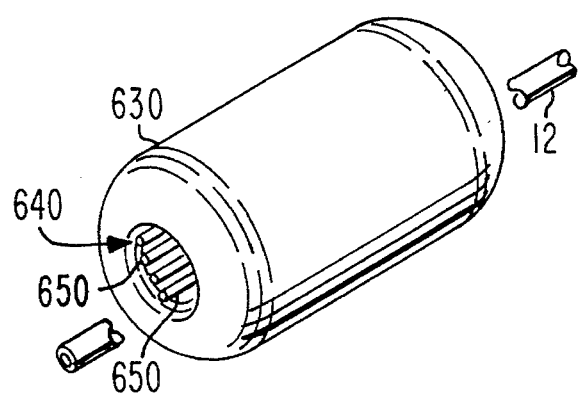
FIG. 6a is a perspective or isometric view.
Figure 6B:
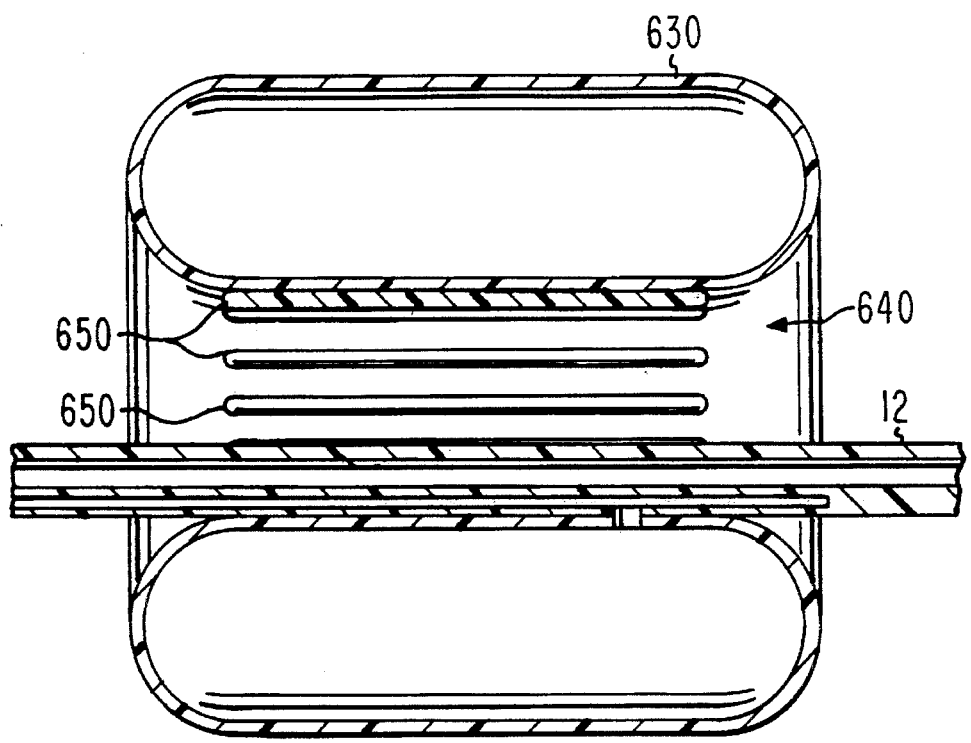
FIG. 6b is a cross-sectional view.
Figure 6C:
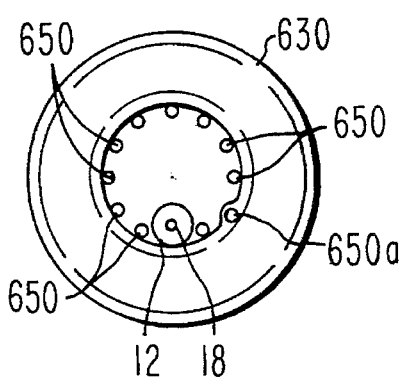
FIG. 6c is an end view with the balloon expanded.
Figure 6D:
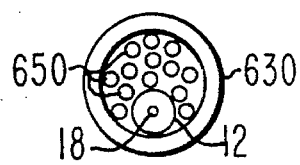
FIG. 6d is an end view with the balloon collapsed, of a catheter including a plurality of elongated reinforcing rods affixed to the periphery of the central channel.

As mentioned above, a completely rigid tube portion of the balloon may make it difficult to collapse the balloon for insertion into a small vas. According to an aspect of the invention, the rigid portion of the peripheral closure of the balloon may have anisotropic rigidity (rigidity which differs when measured in different directions), allowing collapse of the balloon into a small volume, and yet tending to prevent closure of the central channel. FIG. 6a is a perspective or isometric view, FIG. 6b is a cross-sectional view, FIG. 6c is an end view with the balloon expanded, and FIG. 6d is an end view with the balloon collapsed, of a balloon 630 including a central channel 640 and a plurality of elongated reinforcing rods 650 affixed to the periphery of the central channel. The rods 650 and 650a provide the anisotropic rigidity, contributing substantially to rigidity against inward bulging of the balloon along the central channel, by virtue of keeping the same inner diameter of the central channel all along the length of the channel, but offering little or no resistance to collapsing of the reinforcing rods toward each other when the balloon is deflated, as illustrated in FIG. 6d, to make the distal end of the catheter small enough to fit into a vas smaller in diameter than the expanded diameter of the central channel. The folding of the balloon membrane resulting from deflation and collapse is not illustrated in FIG. 6d. Rods 650 and 650a may be made from spring steel, beryllium copper, carbon-fiber reinforced resin, bamboo, or any other strong, biocompatible material.

Figure 6E:
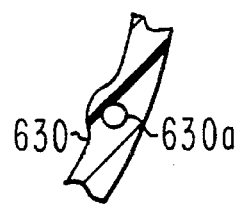
FIG. 6e is a cross-section of a rod, showing an alternative arrangement by which it may be embedded in the balloon material.

FIG. 6e is a cross-sectional view of an alternative embodiment of the arrangement of FIGS. 6a–6d, where the hyphen represents the word "through". In FIG. 6e, rod 650a is seen in cross-section, enclosed within a portion of balloon membrane 630, rather than being affixed to the exterior of the membrane. If balloon membrane 630 of FIG. 6e were made from two thin membranes, the rod could be sandwiched between the two membranes. Encasing the rods in the membrane in this manner may allow the use of a less biocompatible material for the rods, since they are not exposed to body fluids during use.

Figure 7A:
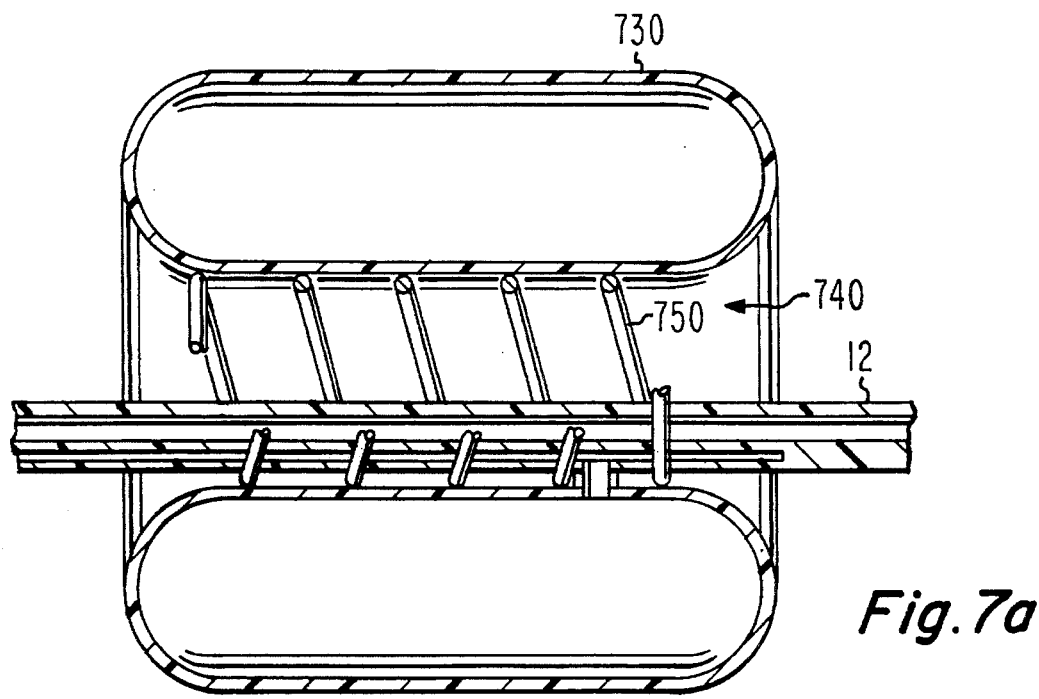
FIGS. 7a, and 7b are simplified cross-sectional side and end views of an inflated balloon catheter according to the invention in which a collapsible spiral reinforcement is used.
Figure 7B:
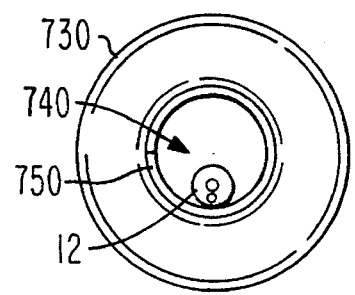
Figure 7C:
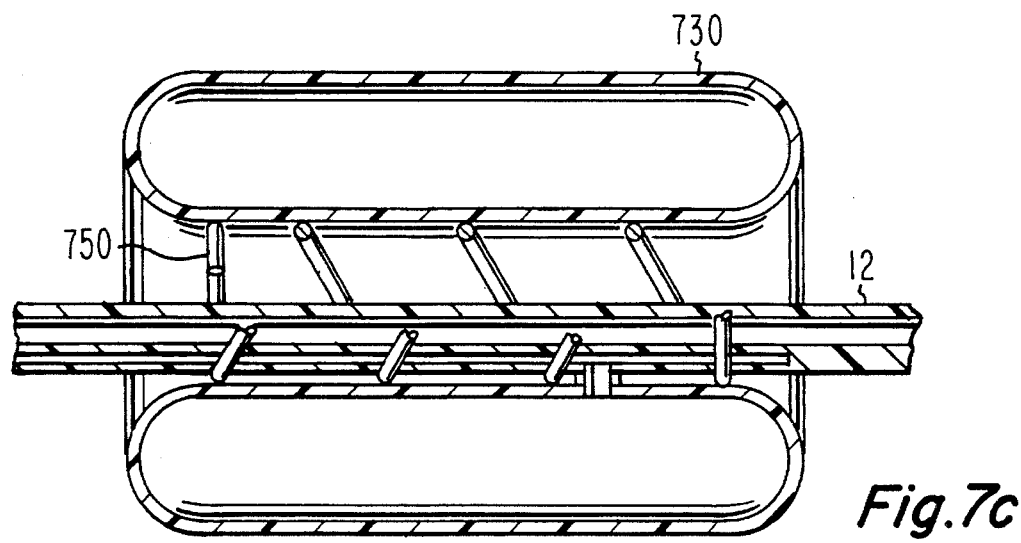
FIG. 7c is a simplified cross-sectional side view of the balloon of FIG. 7a in a partially deflated and collapsed state.

FIG. 7a is a side cross-section of an inflated balloon using a helical coil reinforcement, such as a helical spring. In FIG. 71, 730 represents the peripheral closure, which in this case is a simple elastic membrane having substantially the same rigidity in all portions. The central aperture or channel is designated 740, and the helical spring is designated 750. FIG. 7c illustrates how the helical coil can be collapsed in order to reduce the cross-sectional area of the reinforcement. If the helical reinforcement 750 is affixed to the balloon membrane in the interior of the channel, the reinforcement may only be collapsed when the balloon is at least partially deflated.

Other embodiments of the invention will be apparent to those skilled in the art. For example, the arrangement of FIG. 5 may have a stepped thickness, rather than a tapered thickness; if there is only one step (pair) between the thinnest portion of the balloon peripheral closure and the thickest portion, something akin to the arrangement of FIGS. 2a and 2b is formed, whereas if there are a plurality of step pairs, a stepwise approximation to the arrangement of FIG. 5 is formed. The elongated portion of the catheter may be provided with as many lumens as may be required for the desired purposes, including infusing and aspirating medications and body fluids, and may include fiber optic scopes, transmission lines or electrical conductors for sensing body voltages, or for applying heat or RF, or for other reasons, and may further include optical fibers for carrying laser pulses. As known, the inflation fluids may be liquid or gaseous, and may be radiopaque. While balloon inflation lumen 246 of FIG. 2a is illustrated as extending directly from the balloon interior to balloon inflation lumen 24 adjacent to the balloon, the balloon inflation lumen could extend between inflation lumen 24 and the balloon by way of a separate tube.

What is claimed is:

1. A catheter, comprising:

an elongated portion defining proximal and distal ends and also defining at least one elongated lumen adapted for the flow of fluid therethrough, said elongated portion having a particular cross-sectional area at a particular location near said distal end;

balloon means coupled near said particular location near said distal end of said elongated portion, said balloon means defining a peripheral closure including a relatively elastic membrane portion and a less elastic portion of said balloon means, said peripheral closure defining an interior surface which is adjacent the interior of said balloon, and also defining an exterior surface which is adjacent the exterior of said balloon, said balloon being adapted for inflation within a vas and being configured, when so inflated within a vas, to define an open channel adjacent said exterior surface of said closure, said open channel extending from a distal portion of said balloon to a proximal portion of said balloon, and having a cross-sectional area greater than said particular cross-sectional area of said elongated portion of said catheter, said elongated portion of said catheter extending through said open channel, and being coupled to said peripheral closure on one side of said open channel, whereby body fluids may flow through that portion of said cross-sectional area of said channel which is not occupied by said elongated portion of said catheters, said less elastic portion of said balloon means extending completely about said open channel from said distal portion of said balloon to said proximal portion of said balloon, to thereby tend to prevent closure of said channel when said balloon is inflated; and at least one path for the flow of balloon inflation fluid extending between said elongated lumen defined by said elongated portion and the interior of said balloon, whereby said balloon may be inflated and deflated from said proximal end of said elongated portion of said catheter.

2. A catheter according to claim 1, wherein said membrane of said balloon means defines a surface which, when said balloon means is inflated, is substantially toroidal and defines a central opening, whereby said central opening of said toroidal surface defines said open channel.

3. A catheter according to claim 1, wherein said less elastic portion of said peripheral closure is a substantially rigid tube, the interior of which defines said open channel, and the exterior of which constitutes at least a portion of said inner surface of said balloon.

4. A catheter according to claim 3, wherein said peripheral closure of said balloon means defines a surface which, when said balloon means is inflated, is substantially toroidal and defines a central opening, whereby said central opening of said toroidal surface defines said open channel; and wherein said elongated portion is attached to said interior of said tube on one side of said central opening of said toroidal surface.

5. A catheter according to claim 1, wherein said less elastic portion has anisotropic elasticity.

6. A catheter according to claim 1, wherein said less elastic portion includes a reinforced elastic membrane.

7. A catheter according to claim 6, wherein said reinforcement is anisotropic.

8. A catheter according to claim 7, wherein said central channel defines a channel axis; and said anisotropic reinforcement comprises a plurality of relatively rigid elongated rods, each defining an axis of elongation, said rods being affixed to said peripheral closure at the interior of said open channel, with said axes of elongation mutually parallel and parallel to said channel axis.

9. A catheter comprising:

an elongated portion defining proximal and distal ends and also defining at least one elongated lumen adapted for the flow of fluid therethrough, said elongated portion having a particular cross-sectional area at a particular location near said distal end;

balloon means coupled near said particular location near said distal end of said elongated portion, said balloon means defining a peripheral closure including a relatively elastic membrane portion and a less elastic portion of said balloon means, said less elastic portion including an anisotropically reinforced elastic membrane comprising a plurality of relatively rigid elongated rods, each defining an axis of elongation, said peripheral closure defining an interior Surface which is adjacent the interior of said balloon, and also defining an exterior surface which is adjacent the exterior of said balloon, said balloon being adapted for inflation within a vas and being configured, when so inflated within a vas, to define an open channel, which defines a channel axis, adjacent said exterior surface of said closure, said open channel extending from a distal portion of said balloon to a proximal portion of said balloon, and having a cross-sectional area greater than said particular Cross-sectional area of said elongated portion of said catheter, said rigid elongated rods being affixed to said peripheral closure at the interior of said open channel, with said axes of elongation mutually parallel and parallel to said channel axis, said elongated portion of said catheter extending through said open channel, and being coupled to said peripheral closure on one side of said open channel, whereby body fluids may flow through that portion of said cross-sectional area of said channel which is not occupied by said elongated portion of said catheter;

at least one path for the flow of balloon inflation fluid extending between said elongated lumen defined by said elongated portion and the interior of said balloon, whereby said balloon may be inflated and deflated from Said proximal end of said elongated portion of said catheter; and a relatively inelastic filamentary reinforcement wound about said balloon, passing repeatedly through said central channel and about said exterior surface of said balloon.

10. A catheter according to claim 7, wherein said central channel defines a channel axis, and wherein said anisotropic reinforcement is in the form of a helix centered about said channel axis.

11. A catheter according to claim 10, wherein said helical reinforcement is affixed to said peripheral closure adjacent the interior of said channel.

12. A catheter according to claim 1, wherein said relatively elastic membrane portion is made from polyethylene terephthalate.

13. A catheter according to claim 1, wherein said relatively elastic membrane portion of said peripheral closure is made from a first material, and defines a particular thickness between said interior surface and said exterior surface, and said less elastic portion of said peripheral closure is made from said same first material, and defines a second thickness, greater than said particular thickness, between said interior surface and said exterior surface.

14. A catheter according to claim 13, wherein said thickness tapers from said particular thickness to said second thickness, greater than said particular thickness.

15. A catheter according to claim 1, wherein said path extending between said elongated lumen defined by said elongated portion and the interior of said balloon for the flow of balloon inflation fluid comprises an aperture extending through said peripheral closure and the wall of said elongated portion.

* * * * *